United States Patent [19]
Swartz et al.

[11] Patent Number: 5,846,223
[45] Date of Patent: Dec. 8, 1998

[54] DIAGNOSIS AND TREATMENT OF ATRIAL FLUTTER IN THE RIGHT ATRIUM

[75] Inventors: John F. Swartz, Tulsa, Okla.; John D. Ockuly, Minnetonka; James A. Hassett, Bloomington, both of Minn.

[73] Assignee: Daig Corporation, Minnetonka, Minn.

[21] Appl. No.: 653,649

[22] Filed: May 24, 1996

Related U.S. Application Data

[60] Division of Ser. No. 431,787, May 1, 1995, abandoned, which is a continuation-in-part of Ser. No. 272,014, Jul. 8, 1994, Pat. No. 5,575,766, which is a continuation-in-part of Ser. No. 147,168, Nov. 3, 1993, Pat. No. 5,497,774, and Ser. No. 146,744, Nov. 3, 1993, Pat. No. 5,427,119.

[51] Int. Cl.[6] .................................................. A61M 31/00
[52] U.S. Cl. .............................. 604/53; 604/49; 604/281; 607/115; 607/119
[58] Field of Search ............................... 604/49, 53, 281, 604/284; 607/96, 101, 115, 119, 15; 128/645, 702, 705, 772; 600/15–17

[56] References Cited

U.S. PATENT DOCUMENTS

| | | | |
|---|---|---|---|
| 4,945,912 | 8/1990 | Langberg . | |
| 5,104,393 | 4/1992 | Isner et al. | 606/15 |
| 5,131,406 | 7/1992 | Kaltenbach | 128/772 |
| 5,147,355 | 9/1992 | Friedman et al. | 606/23 |
| 5,171,232 | 12/1992 | Castillo et al. | 604/280 |
| 5,188,619 | 2/1993 | Myers | 604/280 |
| 5,195,942 | 3/1993 | Weil et al. | 600/18 |
| 5,203,776 | 4/1993 | Durfee | 604/264 |
| 5,209,229 | 5/1993 | Gilli | 128/419 D |
| 5,242,441 | 9/1993 | Avitall . | |
| 5,295,484 | 3/1994 | Marcus et al. | 128/660.03 |
| 5,299,574 | 4/1994 | Bower | 128/658 |
| 5,312,341 | 5/1994 | Turi | 604/96 |
| 5,409,019 | 4/1995 | Wilk | 128/898 |
| 5,411,531 | 5/1995 | Hill et al. | 607/14 |
| 5,427,119 | 6/1995 | Swartz et al. | 128/772 |
| 5,575,766 | 11/1996 | Swartz et al. | 604/53 |

OTHER PUBLICATIONS

Singer, I, et al, "Catheter Ablation for Arrhythmias", Clinical Manual of Electrophysiology, pp. 421–431 (1993).

Falk, R.H. et al, "Atrial Fibrillation, Mechanisms and Management" pp. 359–374 (1992).

Horowitz, L.N. "Current Management of Arrhythmias" pp. 373–378 (1991).

Gallagher, J.J. et al. "Catheter Technique for Closed Chest Ablation of the Atrioventricular Conduction System" N. Engl. J. Med., vol. 306, pp. 194–200 (1982).

Tracy, C.M. "Radiofrequency Catheter Ablation of Ectopic Atrial Tachycardia Using Paced Activation Sequence Mapping" J. Am. Coll. Cardiol., vol. 21, pp. 910–917 (1993).

Saul, JP et al. "Catheter Ablation of Accessory Atrioventricular Pathways in Young Patients: Use of Long, Vascular Sheaths, the Transseptal Approach and a Retrograde left Posterior Approach" J. Amer. Coll. Card., vol. 21, No. 3, pp. 571–583 (1993).

Swartz, J.F. et al. "Radiofrequency Endocardial Catheter Ablation of Accessory Atrioventricular Pathway Atrial Insertion Sites" Circulation, vol. 87, No. 2, pp. 487–499 (1993).

*Primary Examiner*—Mark Bockelman
*Assistant Examiner*—Jennifer R. Sadula
*Attorney, Agent, or Firm*—Scott R. Cox

[57] ABSTRACT

A process for the treatment of atrial flutter and/or atrial fibrillation in the right atrium by use of an ablating and/or mapping catheters guided by a guiding introducer. Also disclosed is a predetermined shape for the guiding introducer for use in the treatment of atrial flutter and/or atrial fibrillation in the right atrium.

24 Claims, 5 Drawing Sheets

DIAGNOSIS AND TREATMENT OF ATRIAL FLUTTER IN THE RIGHT ATRIUM

This application is a divisional application of Ser. No. 08/431,787, filed May 1, 1995, now abandoned, which is a continuation-in-part application of application Ser. No. 08/272,014, filed Jul. 8, 1994, now U.S. Pat. No. 5,575,766, which is a continuation-in-part of Ser. No. 08/147,168, filed Nov. 3, 1993, now U.S. Pat. No. 5,497,774 and Ser. No. 08/146,744, filed Nov. 3, 1993, now U.S. Pat. No. 5,427,119.

BACKGROUND OF INVENTION

1. Field of Invention

This invention relates to introducers. More particularly, this invention relates to a guiding introducer for use within the right atrium of the human heart for the treatment of atrial flutter.

2. Prior Art

Introducers and catheters have been in use for medical procedures for many years. For example, one use has been to convey an electrical stimulus to a selected location within the human body. Another use is to monitor and make measurements for diagnostic tests within the human body. Catheters may be used by a physician to examine, diagnose and treat while positioned at a specific location within the body which is otherwise inaccessible without more invasive procedures. In use, catheters may be inserted into a major vein or artery which is near the body surface. These catheters are then guided to the specific location for examination, diagnosis or treatment by manipulating the catheter through the artery or vein of the human body.

Catheters have become increasingly useful in remote and difficult to reach locations within the body. However, the utilization of these catheters is frequently limited because of the need for the precise placement of the tip of the catheter at a specific location within the body.

Control of the movement of catheters to achieve such precise placement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the tip of the catheter reaches the desired location in the heart.

The distal end of a catheter used in such a procedure is sometimes preformed into a desired curvature so that by torquing the catheter about its longitudinal axis, the catheter can be manipulated to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 5,231,994 discloses a guide catheter for guiding a balloon catheter for the dilation of coronary arteries. U.S. Pat. No. 4,117,836 discloses a catheter for the selective coronary angiography of the left coronary artery and U.S. Pat. Nos. 5,215,540, 5,016,640 and 4,883,058 disclose catheters for selective coronary angiography of the right coronary artery. U.S. Pat. No. 5,242,441 discloses a deflectable catheter for ablation procedures in the ventricular chamber. See also U.S. Pat. No. 4,033,331. In addition, U.S. Pat. No. 4,898,591 discloses a catheter with inner and outer layers containing braided portions. The '591 patent also discloses a number of different curvatures for intravascular catheters. Thus, there are a number of patents which disclose catheters with predetermined shapes, designed for use during specific medical procedures generally associated with the heart or the vascular system. Because of precise physiology of the heart and the vascular system, catheters or introducers with precisely designed shapes for predetermined uses within the human heart and vascular system are increasingly important.

Catheter ablation of human type 1 atrial flutter has been disclosed in Feld, Gregory K. *Radiofrequency Catheter Ablation of Cardiac Arrhythmias*, Chapter 25, pages 459–476 (1995). It is believed that type 1 atrial flutter results from a counterclockwise reentry circuit in the right atrium which travels between the inferior vena cava and the tricuspid valve. Dr. Feld proposes the elimination of type 1 atrial flutter by ablation of sites posterior or inferior to the ostium of the coronary sinus between the inferior vena cava and the tricuspid valve using a catheter but without using a shaped sheath or guiding introducer. See also Feld, Gregory K. et al., "Radiofrequency Catheter Ablation for the Treatment of Human Type 1 Atrial Flutter" *Circulation*, Vol. 86, #4, pp. 1223–1240 (Oct. 1992) and Saoudi, N. et al., "Catheter Ablation of the Atrial Myocardium in Human Type I Atrial Flutter" *Circulation*, Vol. 81, #3, pp. 762–771 (March 1990).

Catheter ablation of accessory pathways using a long vascular sheath by means of a transseptal or retrograde approach is discussed in Saul, J. P., et al. "Catheter Ablation of Accessory Atrioventricular Pathways in Young Patients: Use of long vascular sheaths, the transseptal approach and a retrograde left posterior parallel approach" *J. Amer. Coll. Card.*, Vol. 21, no. 3, pps 571–583 (March 1, 1993). See also Swartz, J. F. "Radiofrequency Endocardial Catheter Ablation of Accessory Atrioventricular Pathway Atrial Insertion Sites" *Circulation*, Vol. 87, no. 2, pps. 487–499 (February, 1993).

Atrial fibrillation is the most common sustained heart arrhythmia. It is estimated to occur in upwards of 0.4 percent of the adult population and perhaps as many as 10 percent of the population who are 60 years or older. Cox, J. L., et al., *Electrophysiology, Pacing and Arrhythmia*, "Operations for Atrial Fibrillation," Clin. Cardiol. 14, 827–834 (1991). Atrial arrhythmia may be transient or persistent. While most atrial arrhythmia occurs in individuals having other forms of underlying heart disease, some atrial arrhythmias do not directly cause death as frequently as ventricular arrhythmias. They increase the risk factor for a number of other diseases such as strokes, thrombosis, atherosclerosis, systemic and cerebral embolism and cause a number of additional medical problems.

Certain patients with symptomatic or life threatening atrial arrhythmias cannot be adequately treated by drugs or these medical devices. Other forms of aggressive treatment are mandated, which may include surgery. For example, a surgical procedure for the treatment of atrial arrhythmia known as the "Maze" procedure is disclosed in Cox, J. L. et al., *Electrophysiology, Pacing and Arrhythmia*, "Operations for Atrial Fibrillation," Clin. Cardiol. 14, 827–834 (1991). Other surgical procedures for atrial arrhythmia are disclosed, for example, in Martin, D., et al., *Atrial Fibrillation*, pp. 54–56 (1994).

Another procedure used for certain types of cardiac arrhythmia (but not atrial fibrillation) within the last 10 to 15 years is catheter ablation. This procedure has been used to interrupt or modify existing conduction pathways associated with ventricular arrhythmias within the heart. The particular area for ablation depends on the type of underlying ventricular arrhythmia. The ablation of sites in the right atrium by use of an ablation catheter have been disclosed, as previously discussed, in Feld, Gregory K. et al., "Radiofrequency Catheter Ablation for the Treatment of Human Type 1 Atrial Flutter" *Circulation*, Vol. 86, #4, pp. 1223–1240 (October 1992) and Saoudi, N. et al., "Catheter Ablation of the Atrial Myocardium in Human Type I Atrial Flutter" *Circulation*, Vol. 81, #3, pp. 762–771 (March 1990). In addition, one common ablation procedure is for the treatment of atrioventricular (AV) nodal reentrant tachycardia. With this problem ablation of the fast or slow AV nodal pathways has become an accepted treatment. See Singer, I., et al., "Catheter Ablation for Arrhythmias" *Clinical Manual of Electrophysiology*, pp. 421–431 (1993). The use of ablation catheters for ablating locations within the heart has been disclosed, for example in U.S. Pat. Nos. 4,641,649, 5,263, 493, 5,231,995, 5,228,442 and 5,281,217. However, none utilize a guiding introducer to guide the ablation catheter to a particular location.

U.S. Pat. No. 4,641,649 discloses the use of high frequency energy for the treatment of tachycardia or cardiac dysrhythmia. See also U.S. Pat. Nos. 5,246,438 and 4,945,912 for the use of radiofrequency energy for ablation of cardiac tissue. In addition, various articles have disclosed the ablation of specific locations within the heart by use of energy, in particular, radiofrequency energy. See, for example, Gallagher, J. J. et al. "Catheter Technique for Closed-Chest Ablation of the Atrioventricular Conduction System" N. Engl. J. Med. Vol. 306, pp. 194–200 (1982); Horowitz, L. N. "Current Management of Arrhythmia" pp. 373–378 (1991); Falk, R. H. et al. "Atrial Fibrillation Mechanics and Management" pp. 359–374 (1992); and Singer, I. "Clinical Manual of Electrophysiology" pp. 421–431 (1993).

In addition, the use of radiofrequency ablation energy for the treatment of Wolff-Parkinson-White Syndrome in the left atrium by use of a transseptal sheath is disclosed in Swartz, J. F. et al. "Radiofrequency Endocardial Catheter Ablation of Accessory Atrioventricular Pathway Atrial Insertion Sites" Circulation 87:487–499 (1993). See also Tracey, C. N. "Radio Frequency Catheter Ablation of Ectopic Atrial Tachycardia Using Paced Activation Sequence Mapping" J. Am. Coll. Cardiol. 21:910–917 (1993).

Accordingly, it is an object of this invention to prepare a guiding introducer for selected medical procedures in the right atrium.

It is a further object of this invention to prepare a guiding introducer for use in selected electrophysiology procedures within the right atrium of the heart.

Another object of this invention is to prepare a guiding introducer for use in selected ablation procedures within the right atrium of the heart.

It is a still further object of this invention to prepare a guiding introducer for use in the selected ablation of sites in the right atrium of the heart for the treatment of atrial flutter.

It is a still further object of this invention to prepare a guiding introducer for use in the right atrium as an element of the treatment of atrial arrhythmia including, specifically, atrial fibrillation.

These and other objects are obtained by the design of the guiding introducer system disclosed in the instant invention.

SUMMARY OF INVENTION

The instant invention includes a procedure for the diagnosis and treatment of atrial flutter or atrial fibrillation within the right atrium of the heart comprising (a) introducing into the right atrium a guiding introducer, wherein said guiding introducer contains a lumen running lengthwise therethrough, a proximal and a distal end;

(b) introducing into the lumen of the guiding introducer an ablating or mapping catheter containing a proximal and distal end, wherein said catheter has one or more electrodes located at or near the distal end of the catheter;

(c) guiding the catheter to a selected location within the right atrium by use of the guiding introducer; and (d) mapping and/or ablating a selected location or track within the right atrium by use of the electrodes of the ablation catheter.

The instant invention also discloses a specifically designed shape or shapes for the guiding introducer for use with mapping and/or ablation catheters in the mapping and/or treatment of atrial flutter or atrial fibrillation.

DESCRIPTION OF THE INVENTION

A typical human heart includes a right ventricle, a right atrium, left ventricle and left atrium. The right atrium is in fluid communication with the superior vena cava and the inferior vena cava. The atrioventricular septum separates the atria from the ventricles. The tricuspid valve contained within the atrioventricular septum communicates the right atrium with the right ventricle. The mitral valve contained within the atrioventricular septum communicates the left atrium with the left ventricle. On the inner wall of the right atrium, where it is connected with the left atrium, is a recessed portion, the fossa ovalis. Between the fossa ovalis and the tricuspid valve is the opening or ostium for the coronary sinus. The coronary sinus is a large epicardial vein which accommodates most of the venous blood which drains from the heart itself into the right atrium. See FIGS. 1A and 1B.

In the normal heart, contraction and relaxation of the heart muscle (myocardium) takes place in an organized fashion as electro-chemical signals pass sequentially through the myocardium from the atrial to the ventricular tissue along a well defined route which includes the His-Purkinje system. Initial electric impulses are generated at the sinuatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, patients diagnosed with Wolff-Parkinson-White syndrome have an arrhythmia, the cause of which is believed to be the existence of an anomalous conduction pathway or pathways that connect the atrial muscle tissue directly to the ventricular muscle tissue, thus by-passing the normal His-Purkinje system. These pathways are usually located in the fibrous tissue that connect the atrium and the ventricle.

Three of the most common arrhythmia are ectopic atrial tachycardia, atrial fibrillation and atrial flutter. Atrial fibrillation can result in significant patient discomfort and even death because of a number of associated problems, including: (1) an irregular heart rate which causes the patient discomfort and anxiety, (2) loss of synchronous atrioventricular contractions which interferes with cardiac hemodynamics, resulting in varying levels of congestive heart failure, and (3) stasis of blood flow, which increases the vulnerability to thromboembolism. It is sometimes difficult to isolate a specific pathological cause for the atrial fibrillation although it is believed that the principle mechanism is one or a multitude of reentry circuits within the left and/or right atrium. Efforts to alleviate these problems in the past have included significant usage of pharmacological treatments. While pharmacological treatments are sometimes effective, in some circumstances drug therapy is ineffective and frequently is plagued with side effects such as dizziness, nausea, vision problems and other difficulties.

Another type of atrial arrhythmia is atrial flutter. Atrial flutter is thought to result from a counterclockwise reentry circuit in the right atrium associated with the atrial septum and the right atrial freewall. The reentry circuit normally travels between the inferior vena cava and the tricuspid valve. Studies have demonstrated that the reentry circuit contains an area of slow conduction generally in the low posteroseptal right atrium. Endocardial direct current energy has been used successfully in the treatment of atrial flutter because it produces a large, local area of ablation and generally converts the atrial flutter to sinus rhythm. (See the Saoudi, et al. article.) Dr. Feld in his articles proposes the use of radio frequency energy for the treatment of atrial flutter. In particular, Dr. Feld suggests ablation in two particular sites, posterior or inferior to the ostium of the coronary sinus between the inferior vena cava and the tricuspid valve.

In the last few years surgical procedures have also been utilized in the treatment of atrial arrhythmia. The goal of these surgical procedures parallel that of the pharmacological treatments, to relieve both the subjective symptoms of atrial arrhythmia as well as to normalize hemodynamics by restoring regular atrial contributions to the cardiac output. One method suggested requires isolation of the left atrium from the remainder of the heart by a surgical procedure. See Cox, J. L., et al., "The Surgical Treatment of Atrial Fibrillation," *J. Thoracic and Cardiovascular Surgery*, Vol. 101, No. 4, p. 570 (1991). The initial incisions followed by the scar tissue left by such surgery effectively isolates the left atrium and, in some cases, provides some relief for the patient. Such relief can occur as long as the right atrium maintains adequate sinus rhythm. Various problems associated with this procedure, other than the maintenance of appropriate sinus rhythm, include thromboembolic risks.

Another procedure for treatment of atrial arrhythmia involves the ablating of the His bundle. A permanent pacemaker is then installed, resulting in a regular ventricular beat. See Cox, J. J., et al., "The Surgical Treatment of Atrial Fibrillation," *Journal of Thoracic and Cardiovascular Surgery*, Vol. 101, No. 4, pp. 570–572 (1991). However, because the atria may continue to fibrillate, normal cardiac hemodynamics is not restored and there is still vulnerability to thromboembolism.

A newer surgical procedure for the treatment of atrial arrhythmia designed by Guiraudon in 1985 results in the creation of a narrow corridor between the SA node and the AV node. See Guiraudon, G. M., et al., *Combined Sinoatrial Node/Atrial Ventricular Node Isolation: a Surgical Alternative to His Bundle Ablation in Patients with Atrial Fibrillation*; Circulation 72:(pt-2) III-220 (1985). This procedure isolates a narrow corridor from the remainder of the atrial muscle tissue and can, in some circumstances, alleviate some of the problems associated with atrial arrhythmia.

A more recent, more complex surgical procedure, the "Maze" procedure, has also been designed to treat atrial arrhythmia, particularly atrial fibrillation. See Cox, J. L., et al., "The Surgical Treatment of Atrial Fibrillation," *Journal of Thoracic and Cardiovascular Surgery*, Vol 101, pp. 569–83 (1989). Appropriately placed atrial incisions in the myocardium are designed to interrupt the conduction routes of those areas in the atria that produce the most common reentrant circuits. The procedure is also designed to direct the sinus impulse from the sinus node to the AV node along a specified route. After the procedure, the entire atrial myocardium (except for the atrial appendages and pulmonary veins) is designed to be electrically active by providing for multiple blind alleys off the main conduction route between the SA node and the AV node, thereby preserving atrial transport function postoperatively. While this procedure has resulted in successful treatments for certain patients, there are significant potential risks due to the extensive nature of the surgery.

The effectiveness of the "Maze" procedure is dependent upon the destruction of tissue within the atrium along specific lines or tracks to prevent the formation of reentry circuits while still allowing the atria to contract and permitting the return of normal atrio-ventricular conductivity. It has been discovered that similar success can be achieved without invasive surgery by the use of ablation procedures performed within the atria. However, to accomplish this procedure the ablation catheter must be positioned at predetermined locations within the atria to ablate a predetermined location or tracks within the atria, thus forming a natural barrier to the formation of the reentry circuits. In addition to the necessity of producing ablation tracks in well defined areas of atria, it is also critical for proper transmural lesion formation that adequate contact pressure be maintained between the ablation catheter electrode and the heart tissue to be ablated.

The ablation catheters used to perform the ablation procedures produce scar tissue at the selected site within the atria. The energy necessary to scar or ablate the tissue can be provided by a number of different sources. Originally direct current was utilized to provide the energy for ablation procedures. More recently the preferred choice of energy source has been radio frequency energy (R.F.). Laser, microwave, ultrasound and direct current energy procedures including low energy direct, high energy direct and fulgutronization procedures have also been utilized or are being considered for ablation procedures. The preferred source of energy for the ablation procedures of the instant invention is RF energy.

Individual applications of ablation energy are frequently unsuccessful at blocking the reentrant circuit, and the ablation procedures may have to be repeated several times. This may be because the catheter electrode is not positioned correctly at the beginning of the energy application or that the catheter electrode moves during the attempted ablation. Another problem can be that even though the catheter electrode is located correctly, there may not be enough contact pressure between the tissue to be ablated and the electrode to facilitate sufficient current to flow through the tissue to properly ablate said tissue. The procedure may also be very time consuming. In addition, it may require catheter exchanges to replace a defective or inappropriately selected catheter. To effectively ablate the atrial tissue, the ablation catheter must be positioned precisely within the atrium and maintained in contact with the atrial tissue throughout the energy application. Such procedures may require the ablation electrode of the ablation catheter to remain in contact with the atrial tissue for an extended period of time.

Currently, the most common approach for the positioning of an ablation catheter in the right atrium calls for the introduction of the medical device into the right femoral vein and advancement up through the inferior vena cava into the right atrium. Although a superior approach to the right atrium can also be used, for purposes of the guiding introducer of the instant invention, the inferior approach through the inferior vena cava is required.

Mere introduction of the ablation and mapping catheter into the right atrium is not sufficient to effectively and efficiently perform the ablation procedures on the reentry circuits. The medical practitioner commonly monitors the introduction of the catheter and its progress through the vascular system by a fluoroscope. Such fluoroscopes can not easily identify the specific features of the heart in general, and the critically important structures of the right atrium in specific, thus making placement of the ablation electrode difficult. This placement is especially difficult as the beating heart is in motion. In addition, the catheter will be moving within the right atrium as blood is being pumped through the heart throughout the procedure. Further, because of the difficulty of properly locating the catheter, extended exposure to fluoroscopy may be inevitable. However, such excessive exposure is certainly undesirable.

Figure 2A:
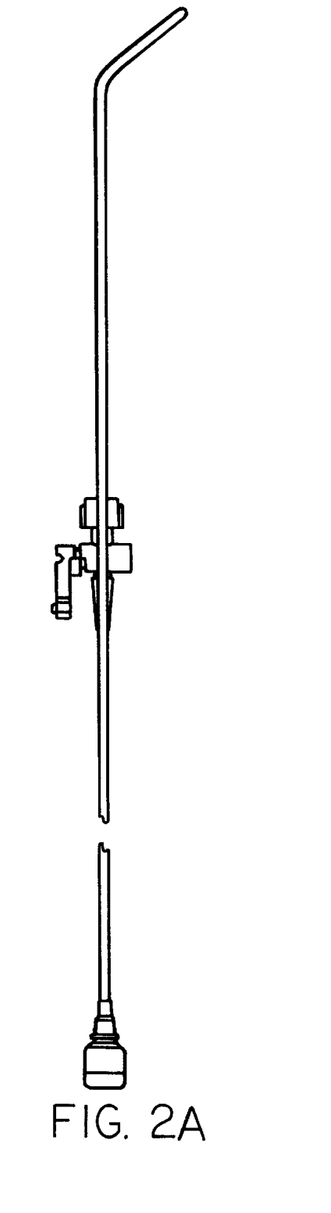
FIG. 2A is a side view of the guiding introducer for use in the treatment of atrial flutter or atrial fibrillation in the right atrium, wherein the side port tubing attached to the proximal end of the guiding introducer is located directly behind the first section of the guiding introducer.
Figure 2B:
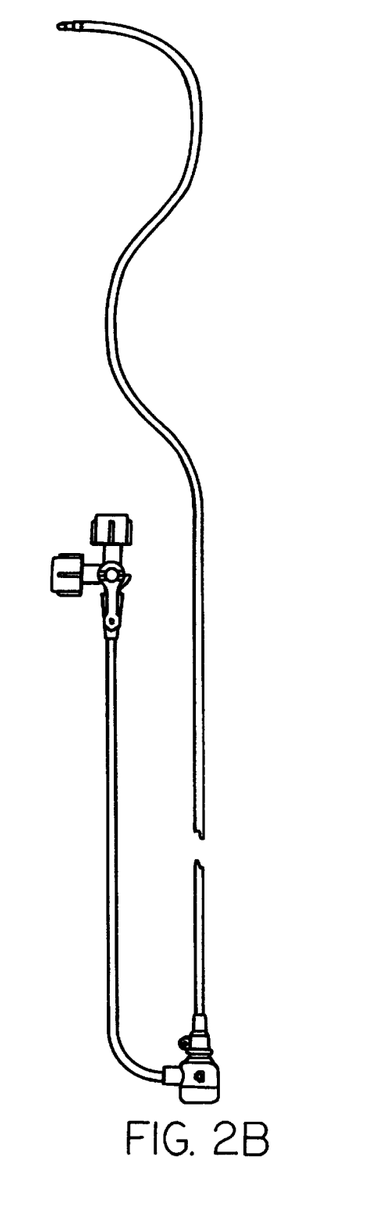
FIG. 2B is a side view of the guiding introducer of FIG. 2A rotated 90° clockwise from the position of FIG. 2A, when viewed from the perspective of the proximal end of the guiding introducer, such that the side port is directed to the left of the guiding introducer.
Figure 2C:
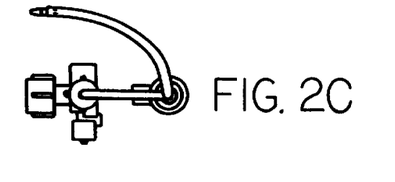
FIG. 2C is an end view of the guiding introducer viewed from the top of the guiding introducer such that the side port tubing is directed to the left of the guiding introducer.

The guiding introducer system of the instant invention addresses and solves these problems. Referring now to FIGS. 2A, 2B and 2C, the guiding introducer of the present invention for use in the right atrium for the treatment of atrial flutter (and also for the treatment of atrial fibrillation) is comprised of a first, second and third sections. (Each section is preferably formed as an integral portion of the entire guiding introducer without discrete divisions. However, the division of the guiding introducer into different sections for discussion better illustrates the overall shape of the guiding introducer.) The guiding introducer will be shown in three views. In each of the views for ease of analysis, the guiding introducer will be secured to a valve for attachment to a conventional side port tubing and stop cock. In each such arrangement, the shape of the guiding introducer and each of its sections will be described, making reference to its position in relation to the side port and side port tubing, where the proximal end of the guiding introducer is secured to the side port tubing. In the first referenced figure (FIG. 2A), the side port tubing is viewed as if it is behind the first section of the guiding introducer. In the second figure (FIG. 2B) the guiding introducer is rotated clockwise about the axis of the first section of the guiding introducer when viewed from the perspective of the proximal end of the guiding introducer. In the third figure (FIG. 2C) the guiding introducer is rotated upwards around the distal end of the guiding introducer.

The first section of the guiding introducer is a conventional, elongated, hollow, generally straight section of sufficient length for introduction into the patient and for manipulation from the point of insertion to the specific desired location within the heart. (The overall length of the first section as shown in FIGS. 2A and 2B has been reduced for ease of illustration.)

Merged with the distal end of the first section of the guiding introducer is the second section which is a generally C-shaped section, curving to the left and then back to the right to a point where it meets with what would have been the first section, if that first section had been extended. See FIG. 2B. The purpose of this second section is to rest against one side of the inferior vena cava at the same time as a portion of the first and third sections rest against the opposite side of the inferior vena cava. Its overall shape is not particularly critical. However, in a preferred embodiment, this second section is comprised of three portions. The first portion curves first to the left in a curved segment as shown in FIG. 2B in a radius from about 0.75 to about 1.75 in. and preferably from about 1.00 to about 1.50 in. The extent of the arc of this curved segment is from about 30 to about 90 degrees and preferably from about 30 to about 60 degrees. Following the curving of this curved segment to the left, the second section then curves back to the right in a second curved segment with a radius from about 0.75 to about 1.75 in. and preferably from about 1.00 to about 1.50 in. The extent of the arc of this second curved segment is from about 30 to about 90 degrees and preferably from about 30 to about 60 degrees of arc. In a preferred embodiment, both the first and the second curved segments of this first portion are generally coplanar (within about 15 degrees of coplanar). At the distal end of this first portion of the second section begins the second portion which is a straight section from about 0.1 to about 2.0 in. and preferably from about 0.1 to about 0.5 in. The overall length of this second section is not critical and it may, in fact, be eliminated, if desired. If the first section of the guiding introducer were extended, this second straight portion would be about 0.5 to about 2.0 in., and preferably from about 0.5 to about 1.5 in., away from the first section extended. Preferably, this straight second portion is also coplanar with the first portion. At the distal end of this second portion begins the third portion of the second section. This third portion is preferably a mirror image of the first portion, curving first to the right and then back to the left as shown in FIG. 2B. The radii and the curvature of the arc of this third portion are approximately the same as those of the first portion of the second section only in reverse.

At the distal end of this second portion, the guiding introducer returns generally to a position that would correspond with the first section of the guiding introducer if that first section were extended.

The distance from the proximal end of the first portion of the second section to the distal end of the third portion of the second section is about 2.0 to about 7.0 in. and preferably 3.5 to about 5.0 in. in length. The overall length of this second section is not particularly critical. While in a preferred embodiment the first, second and third portions of the second section are co-planar (within about 15 degrees of coplanar), alternatively, the first, second and third sections may be out-of-plane with each other. The overall shape of this second section is not particularly critical as long as a portion of the second section is about 0.5 to about 2.0 in., and preferably from about 0.5 to about 1.5 in., away from an extension of the first section if extended. The purpose of this second section is to fit against one side of inferior vena cava while a portion of the first section and the third section of the guiding introducer rests against the opposite side of the inferior vena cava, thereby providing support for the guiding introducer while it is in the inferior vena cava. Although the second section is preferably a pair of curved portions surrounding a short straight portion, alternatively three or more separate curved portions, each with the same or different curvatures and radii, can be used alone or in combination with one or more straight portions, or no straight portion at all, as long as the combination of separate curves and straight portions creates a device that rests against both sides of the inferior vena cava.

The first and second sections are preferably coplanar (within about 15 degrees of coplanar).

The third section of this guiding introducer is also divided into three portions. Preferably, the first portion begins with a straight segment from about 0.1 to about 3.0 in. and preferably from about 0.1 to about 0.5 in. in length. Depending on the length of the straight portion of the second section and the overall length of the second section, the length of this first straight portion can vary dramatically. In fact, no first straight portion need exist at all. The first portion then curves to the right, preferably out of the plane of the first and second sections as shown in FIG. 2A with a radius from about 0.2 to about 1.0 in. and preferably from about 0.3 to about 0.7 in. The extent of the arc of this curve is from about 20 to about 90 degrees and preferably from about 40 to about 60 degrees. The distal end of this first portion of the third section begins the second portion of the third section wherein the guiding introducer curves to the left as shown in FIGS. 2B and 2C. The curve of this second portion has a radius from about 0.5 to about 1.5 in. and preferably from about 0.8 to about 1.2 in. with an arc of the curve from about 45 to about 135 degrees, and preferably from about 70 to about 110 degrees of arc, ending in the third portion of the third section. The third portion of the third section is a straight section from about 0.1 to about 2.0 in. in length and preferably, from about 0.2 to about 1.0 in., ending in the distal tip of the guiding introducer. As with other straight portions of the guiding introducer, the overall length of this straight, third portion can vary dramatically or can even be eliminated, if desired. As with the second section of the guiding introducer, a plurality of curves and straight portions can replace the curved portions and straight portion of the preferred embodiment of the third section of the guiding introducer as long as the combination of curves and straight sections creates generally the same overall curvature of the third section.

The distal tip of the guiding introducer may be, and preferably will be, tapered to form a good transition with a dilator. This tapering is preferably less than 10° and more preferably about 4° to about 7°. The guiding introducer preferably also contains one or a plurality of radiopaque tip marker bands near the distal tip of the guiding introducer. This guiding introducer also preferably contains one or a plurality of vents near the distal tip of the guiding introducer, preferably three or four such vents. The vents are preferably located no more than about 1.00 in. from the distal tip of the guiding introducer and more preferably 0.10 to about 1.00 in. from the distal tip. The size of these vents should be in the range of about 40 to about 60/1000 of an inch in diameter. These vents are designed to prevent air from entering the guiding introducer caused by the withdrawal of the catheter contained within the guiding introducer in the event the distal end of the guiding introducer is occluded. For example, if the tip of the guiding introducer is placed against the myocardium and the catheter located within the guiding introducer is withdrawn, a vacuum may be created within the guiding introducer if no vents are provided. If such vacuum is formed, air may be forced back into the guiding introducer by the reintroduction of a catheter into the lumen of the guiding introducer. Such air could cause significant problems in the patient, including the possibility of a stroke, heart attack or other such problems common with air embolisms. The addition of vents near the distal tip of the guiding introducer prevents the formation of such vacuum by permitting fluid, presumably blood, to be drawn into the lumen of the guiding introducer as the catheter is being removed from the guiding introducer, thus preventing the creation of a vacuum which could cause air to enter the guiding introducer.

The guiding introducer may be made of any material suitable for use in humans which has a memory or permits distortion from, and substantial return to, the desired three dimensional shape. For the purpose of illustration and not limitation, the internal diameter of the guiding introducer may vary from about 6 to about 12 "French" respectively (1 French equals ⅓ of a millimeter). Such guiding introducer can also accept dilators and appropriate guidewires. Obviously, if larger or smaller dilators or catheters are used in conjunction with the guiding introducer of the instant invention, modifications in size or shape can be made to the guiding introducer.

Variations in size and shape of the guiding introducer are also intended to encompass pediatric uses, although the preferred uses are for adult human hearts. It is well recognized that pediatric uses may require reductions in size of the various sections of the guiding introducer, in particular the first section, but without significant modifications to the shape or curve of the guiding introducer.

In addition, variations in size or shape of the guiding introducer are also intended to encompass the specialized situations that sometimes occur in patients with enlarged or rotated hearts.

In operation, a modified Seldinger technique is normally used for the insertion of the catheter into the right femoral vein. The appropriate vessel is accessed by needle puncture. A soft flexible tip of an appropriately sized guidewire is then inserted through, and a short distance beyond, the needle into the vessel. Firmly holding the guidewire in place, the needle is removed. The guidewire is then advanced through the vein up to the inferior vena cava and into the right atrium. With the guidewire in place, a dilator is then placed over the guidewire with the guiding introducer placed over the dilator. The dilator and guiding introducer generally form an assembly to be advanced together along the guidewire into the right atrium. After insertion of the guiding introducer, the guidewire and dilator are then withdrawn. The catheter to be used for treatment of atrial flutter or atrial fibrillation is advanced through the lumen of the guiding introducer and is placed at an appropriate location in the right atrium.

By movement of the guiding introducer in conjunction with fluoroscopic viewing, the distal portion of the guiding introducer can be manipulated to direct the distal end of a catheter placed within the lumen of the guiding introducer to a specific internal surface within the right atrium. In addition, by providing sufficient rigidity, the distal end of the guiding catheter can be maintained in that fixed location or surface position of the endocardial structure to permit the appropriate procedures to be performed. If sensing procedures are involved, the guiding introducer is maneuvered to the desired location. At that point, the electrical activity of the heart peculiar to that location can be precisely determined by use of an electrophysiology catheter placed within the guiding introducer. Further, as the guiding introducer permits precise location of catheters, an ablation catheter may be placed at a precise location for destruction of the cardiac tissue by the use of energy, for example, radio frequency, thermal, laser or direct current (high energy direct, low energy direct and fulgutronization procedures). Preferably, radio frequency energy is utilized for the ablation procedure.

Figure 1A:
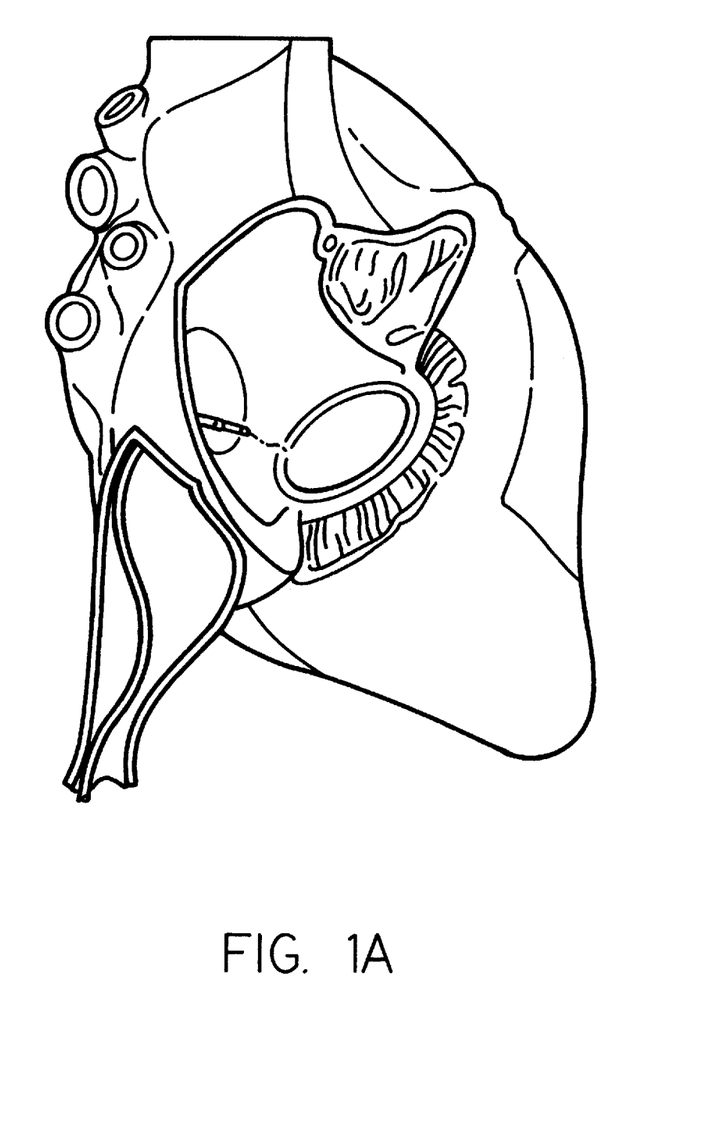
FIG. 1A is a cut away view of the heart with a portion of the inferior vena cava also cut away showing the guiding introducer of the instant invention supporting a catheter for an ablation and/or mapping procedure in the right atrium.
Figure 1B:
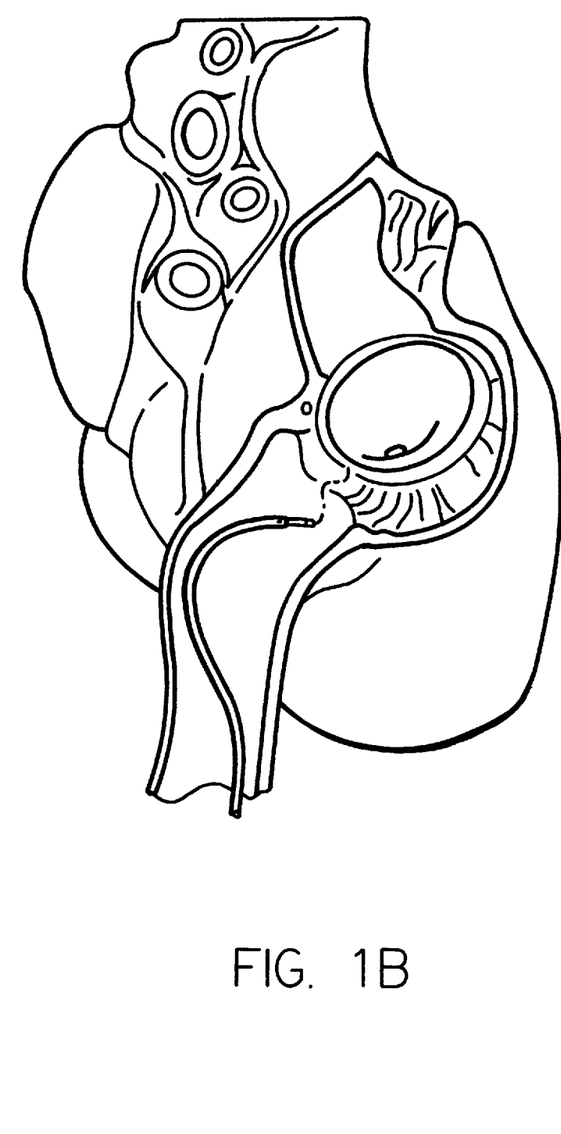
FIG. 1B is a cut away view of the heart with a portion of the inferior vena cava also cut away showing the guiding introducer of the instant invention supporting a catheter for an ablation and/or mapping procedure in the right atrium between the tricuspid valve and the inferior vena cava and down into the inferior vena cava.

The ablation procedures for ablation of atrial flutter are best shown in FIGS. 1A and 1B. In each, the guiding introducer of the instant invention directs the ablation catheter to the lip of the inferior aspect of the tricuspid valve, across the isthmus of tissue between the tricuspid valve and the inferior vena cava and down into the inferior vena cava past the transition point between contractile myocardium and the vascular wall of the inferior vena cava. By this procedure a block in a counterclockwise reentry circuit in the right atrium is formed, thus eliminating the reentry circuit which is thought to cause atrial flutter.

The precise placement of the ablation catheter electrode is important as there will be no dilution of the energy delivered due to unfocused energy being dissipated over the entire cardiac chamber and lost in the circulating blood by a constantly moving tip of the ablating catheter. This guiding introducer permits a significantly reduced amount of energy to be applied while still achieving efficient ablation. Further, time used to perform the procedure is significantly reduced over procedures where no guiding introducer is used. This reduction in time also reduces the amount of fluoroscopy that is necessary for the procedure. The precise placement of the ablation catheter within the right atrium is particularly important because of the difficulties associated with the ablation of atrial flutter.

Figure 1C:
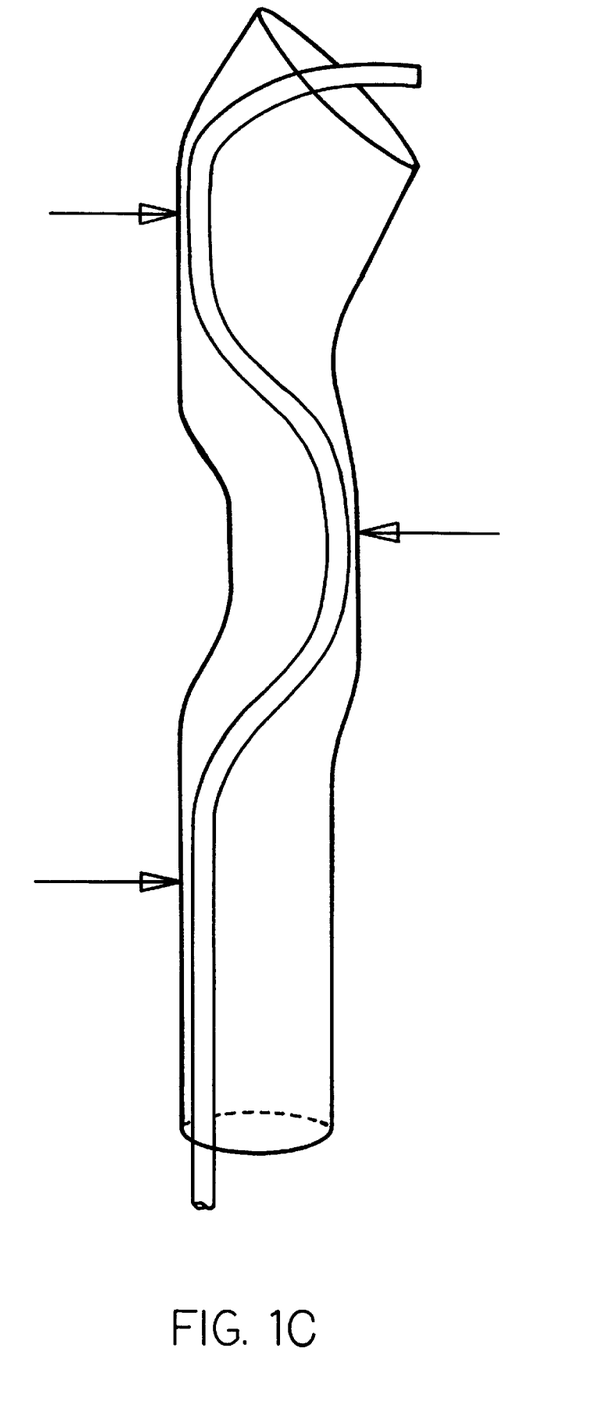
FIG. 1C is a side view of the guiding introducer of the instant invention within the inferior vena cava.
Figure 1D:
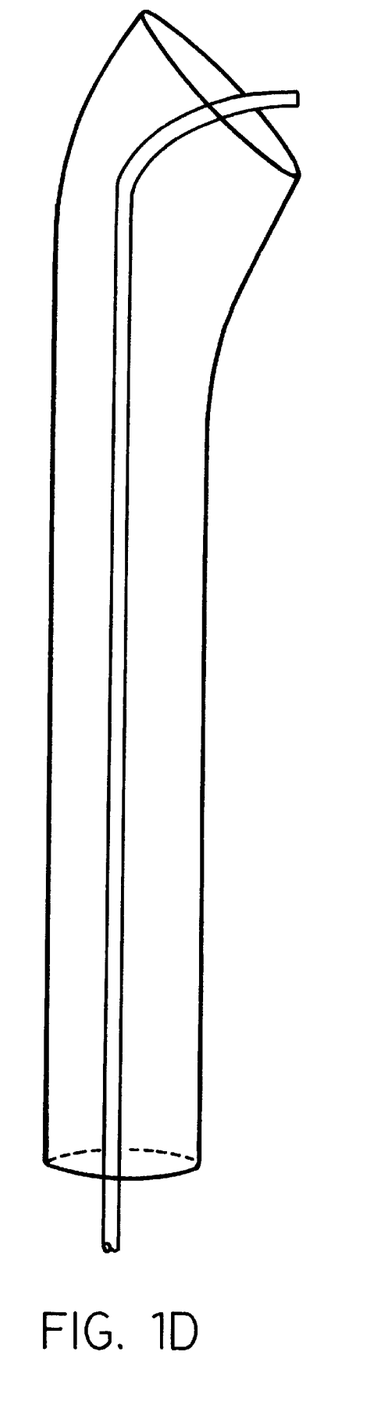
FIG. 1D is a side view of a comparison guiding introducer disclosed in FIGS. 5A and 5B of U.S. Pat. No. 5,575,766.

In addition to the use of the guiding introducer of the instant invention for the treatment of atrial flutter, this guiding introducer may also be used in the treatment of atrial fibrillation. In copending application Ser. No. 08/272,014, which is incorporated into this application by reference, a procedure for the treatment of atrial fibrillation by using guiding introducers and ablation catheters is disclosed. In that procedure a number of different ablation tracks are formed in the left and right atria, each of which is designed to eliminate specific reentry circuits which are thought to cause atrial fibrillation. One of the ablation procedures that is performed as an element of the treatment of atrial fibrillation in the copending application is the ablation of a track between the tricuspid valve and the inferior vena cava. This track, as shown in the copending application in FIG. 3E is referred to as "track five." The guiding introducer of the instant invention is an alternative for the guiding introducer disclosed in the copending application in FIGS. 5A and 5B. In particular, the addition to the guiding introducer of the copending application of the generally C-shaped bend, referred to as the second section of the instant guiding introducer, assists in holding the guiding introducer of the instant invention in a fixed location within the inferior vena cava. (In contrast, the guiding introducer of the copending application without the generally C-shaped bend is shown in FIG. 1D.) As is shown in FIG. 1C, this bend, comprising the second section of the guiding introducer acts to hold the guiding introducer in place against one side of the inferior vena cava while a portion of the first section and the third section of the guiding introducer of the instant invention are held against the opposite side of the inferior vena cava, thus providing a secure platform for an ablation catheter to create the appropriate ablation track across the isthmus between the tricuspid valve and the inferior vena cava.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A procedure for the diagnosis or treatment of atrial flutter or atrial fibrillation in the right atrium of the heart comprising
   (a) introducing into a specific location in the right atrium a guiding introducer with a predetermined shape containing a lumen running lengthwise therethrough, a proximal and a distal end,
   (b) introducing into the lumen of the guiding introducer an ablating or mapping catheter containing a proximal and distal end, wherein said catheter has one or more electrodes located at or near the distal end of the catheter,
   (c) guiding the catheter to a selected location within the right atrium by use of the guiding introducer, and
   (d) mapping or ablating a selected location or track within the right atrium by use of the electrodes of the catheter to treat atrial flutter or atrial fibrillation.

2. The procedure of claim 1 wherein the ablating procedure utilizes one of the following sources of energy: direct current, including high energy direct current, low energy direct current or fulgutronization procedures, microwave, ultrasound, laser, and radio frequency.

3. The procedure of claim 1 wherein the guiding introducer comprises a first, second and third section.

4. The procedure of claim 3 wherein the first section of the guiding introducer is an elongated, hollow, generally straight section of sufficient length for introduction into the patient and for manipulation from the point of insertion through to a desired location within the heart.

5. The procedure of claim 3 wherein the second section of the guiding introducer comprises a first, second and third portion.

6. The procedure of claim 5 wherein the first portion of the second section comprises a first curved segment, curving with an overall arc of about 30 to about 90 degrees followed by a second curved segment, curving generally in the opposite direction from the first curved segment curving with a an overall arc of about 30 to about 90 degrees.

7. The procedure of claim 5 wherein the second portion of the second section comprises a straight portion from about 0.1 to about 2.0 in. in length.

8. The procedure of claim 5 wherein the third portion of the second section comprises a first curved segment curving in an overall arc of about 30 to about 90 degrees followed by a second curved segment curving generally in the opposite direction from the first curved segment with an overall arc of about 30 to about 90 degrees.

9. The procedure of claim 7 wherein the distance from the straight portion of the second section to the first section is from about 0.5 to about 2.0 inches.

10. The procedure of claim 3 wherein the first and second sections are substantially coplanar.

11. The procedure of claim 3 wherein the overall lineal length of the second section if from about 2.0 to about 7.0 in.

12. The procedure of claim 3 wherein the second section of the guiding introducer comprises one or more straight portions and one or more curved portions.

13. The procedure of claim 3 wherein the third section comprises a first, second and third portion.

14. The procedure of claim 13 wherein the first portion of the third section comprises a straight segment from about 0.1 to about 3.0 in. in length and a curved segment, curving in an overall arc of about 20 to about 90 degrees.

15. The procedure of claim 13 wherein the first portion of the third section curves out of a plane formed by the first and second sections of the guiding introducer from about 20 to about 90 degrees.

16. The procedure of claim 13 wherein the second portion of the third section is a curved portion, curving from about 45 to about 135 degrees.

17. The procedure of claim 13 wherein the second portion of the third section curves out of a plane formed by the first and second sections of the guiding introducer from about 20 to about 90 degrees.

18. The procedure of claim 13 wherein the third portion of the third section is a generally straight portion from about 0.2 to about 2.0 inches ending in the distal tip of the guiding introducer.

19. The procedure of claim 3 wherein the third section comprises a first and second portions.

20. The procedure of claim 19 wherein the first portion of the third section comprises a straight segment from about 0.1 to about 3.0 in. in length, followed by a curved segment, curving in an overall arc of about 20 to about 90 degrees.

21. The procedure of claim 19 wherein the first portion of the third section curves out of a plane formed by the first and second sections of the guiding introducer from about 20 to about 90 degrees.

22. The procedure of claim 19 wherein the second portion of the third section is a curved portion, curving from about 45 to about 135 degrees.

23. The procedure of claim 19 wherein the second portion of the third section curves out of a plane formed by the first and second sections of the guiding introducer from about 20 to about 90 degrees.

24. The procedure of claim 3 wherein the third section of the guiding introducer comprises one or more straight sections and one or more curved sections.

* * * * *